United States Patent [19]

Nicholson

[11] Patent Number: Plant 6,320

[45] Date of Patent: Oct. 4, 1988

[54] DOGWOOD TREE "DAYBREAK"

[75] Inventor: Hubert A. Nicholson, Decherd, Tenn.

[73] Assignee: Commercial Nursery, Inc., Decherd, Tenn.

[21] Appl. No.: 924,750

[22] Filed: Oct. 28, 1986

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Frank B. Robb

[57] ABSTRACT

A white flowering Dogwood having distinct olive green leaves with a yellow white margin and fall foliage of distinct color which is borne on an unusually vigorous tree that is more resistant to anthracnose than other variegated leaf dogwood trees.

2 Drawing Sheets

This invention relates to a new and distinct variety of improved variegated leaved, white flowering Dogwood being particularly noted for the distinctly olive green leaves with a yellow white margin, colorful fall foliage borne on an unusually vigorous tree, which is more resistant to anthracnose disease than other variegated leafed Dogwood trees.

My new variety is a chance seedling which was grown under cultivated conditions in Franklin County, Tenn. and I have caused it to be asexually reproduced by budding since that time with the variegations and leaf markings being established and coming true from generation to generation.

Some of the important improvements provided by this new variety are the fact that the resistance to anthracnose disease is observed where it is grown under similar conditions to those varieties which are subject to this disease. In the tree of my new variety white margins on the leaves are held until cooler weather without scorching as is true on "Welchii" (an unpatented variety).

When cooler weather is prevalent the white margins take on a pink color that turns to red as fall advances.

The green in the leaves turns red and purple and the tree as a whole is a more vigorous grower than "Rainbow" U.S. Plant Pat. No. 2,743.

A detailed description of many of the aspects of my new variety follows hereafter with reference being made to the drawing wherein color designations provided are from The Royal Horticultural Society Colour Charts with the more common names established by the National Bureau of Standards referred to the NBS color chip numbers in parenthesis.

The illustration in the accompanying drawing is made by the usual photographic process and as such is subject to the variations which are not able to be controlled but is as nearly representative of the color disclosures as is possible to make the same by such process, and as referred to by the figure numbers as follows.

Figure 1:
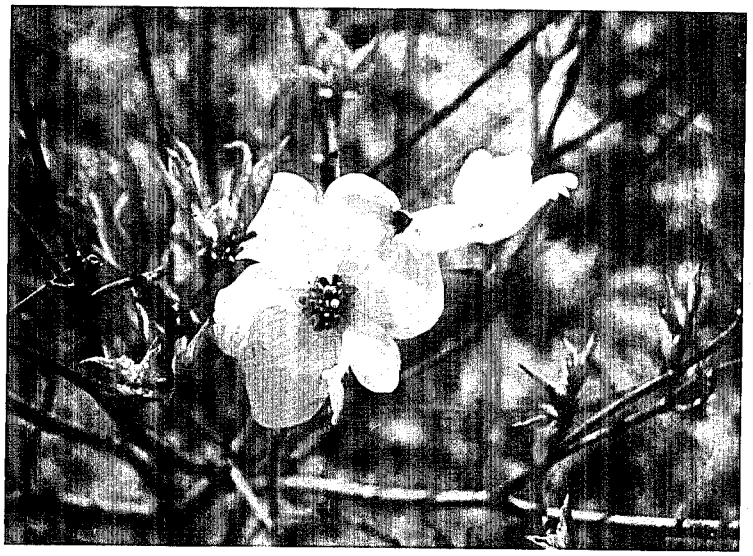
FIG. 1 shows a typical early spring bloom.
Figure 2:
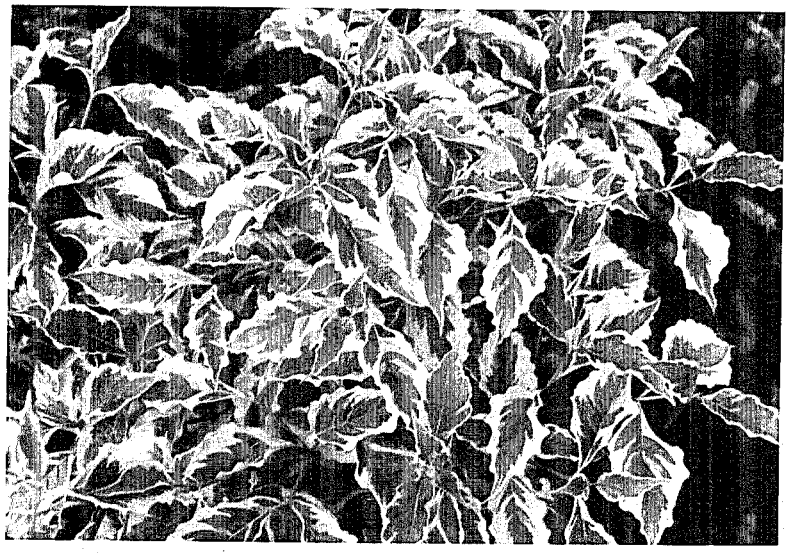
FIG. 2 shows summer foliage.
Figure 3:
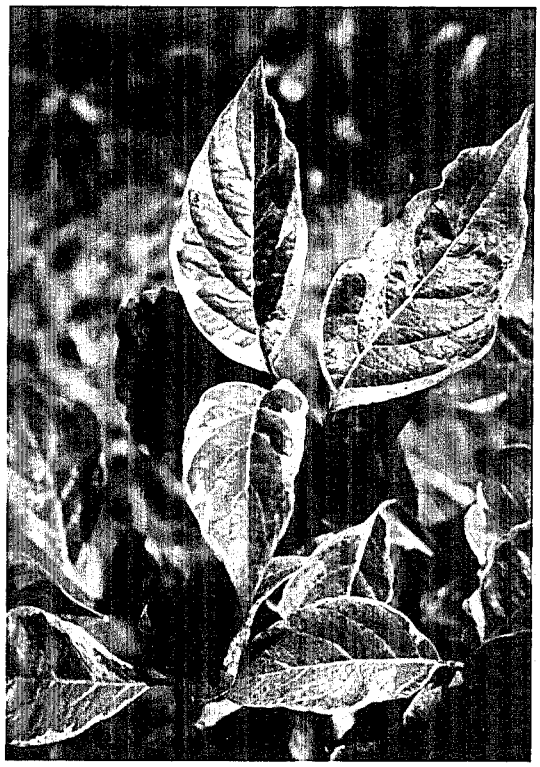
FIG. 3 shows typical early fall color of leaves.
Figure 4:
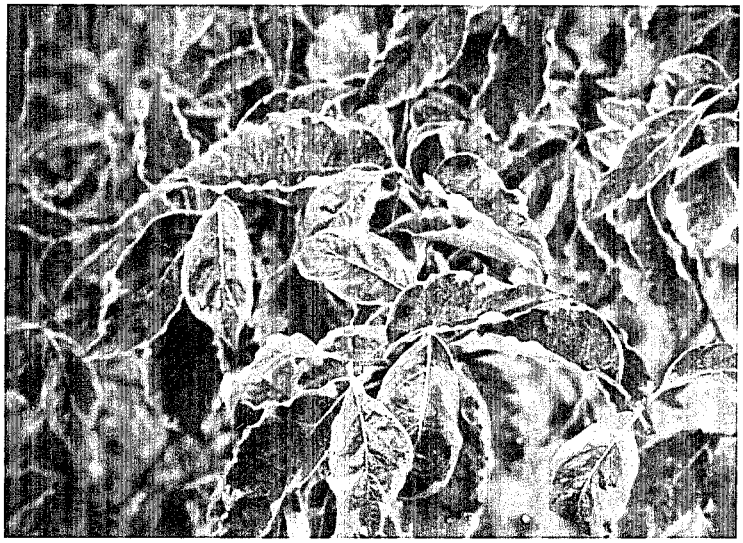
FIG. 4 shows late fall color of leaves.

Specimens described herein were grown under cultivated conditions in Franklin County, Tenn.:

Parentage: Newly found seedling of Cornus, Fla.

Tree: Medium; upright and spreading; tall; hardy.

*Trunk.*—Stocky and smooth.

*Branches.*—Smooth.

*Color.*—Very dark red.

*Leaves.*—Normal quantity; medium thickness. Length — 7 to 10 cm. ovate; 4 to 6 cm. wide. Shape — Ovate. Color — Moderate olive green. Margin — Smooth edge with yellow white margin. Petiole — Medium length.

Flower buds: Hardy to zone 4 and 5.

*Size.*—Normal, 0.5 to 0.75 cm.

*Shape.*—Roundish rising to a point in center.

*Color.*—Grayish green.

Flowers: 4 Bracts each 3 to 4 cm. long.

*Date of first bloom.*—April 15–20.

*Date of full bloom.*—April 18–23.

*Quantity.*—Abundant.

*Size.*—Large.

Petalage (Petal-like bracts):

*Number.*—4.

*Shape of bracts.*—Obovate; notched.

*Size of bracts.*—Large; length — 3 to 4 cm.; width — 1.5 to 3 cm.

Fruit:

*When borne.*—Fall.

*Abundance.*—Average.

*Size.*—0.5 to 1 cm. oval shape.

*Color.*—Bright red.

The various aspects of the new variety which are important to note are supplied in the following description relating to the same wherein the growth habit of the plant is very vigorous under good growing conditions and more vigorous than "Welchii" (variegated) (unpatented) and other Variegated Dogwoods and less susceptible to anthracnose disease, holding its white summer leaf margin until fall with no leaf scorch as on"Welchii".

My new variety blooms at the same time as other Cornus Florida Dogwood with white bracts 7 to 10 cm. across.

The summer foliage is described as being moderate olive green 146B(125m.ol.G) with a margin of yellow white 158B(92y.White); varying in width from 15 to 1.5 cm.; having an irregular outer edge and occasionally indented to the midrib.

The fall foliage is a moderate olive green 146B(125m.ol.G) with pale pink margin 48D(7p.Pk) with yellowish cast to light moderate red 48A(15light m.Red) the mature fall foliage being a very deep red 183C-D(17v.d.Red) with a margin of strong red 51A(12s.Red).

The flower color is a clean white color having a bloom 7 to 10 cm. across.

I claim:

1. A new and distinct variety of Dogwood Tree, substantially as herein shown and described, characterized particularly as to novelty by the unique combination of an irregular yellow white margin on olive green leaves and fall color of very deep red with a margin of strong red, being stronger growing and more resistant to anthracnose disease than other variegated dogwoods which have been observed growing in the same area under similar growing conditions, being a very vigorous grower and more vigorous than "Welchii" or "Rainbow".

* * * * *